United States Patent
Ohishi et al.

(10) Patent No.: US 8,563,743 B2
(45) Date of Patent: Oct. 22, 2013

(54) BENZOFURANONE COMPOUND AND PHARMACEUTICAL COMPOSITION CONTAINING SAME

(75) Inventors: Yoshitaka Ohishi, Ashiya (JP); Takao Toda, Osaka (JP); Seiichi Takeda, Osaka (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 13/810,796

(22) PCT Filed: May 17, 2011

(86) PCT No.: PCT/JP2011/061266
§ 371 (c)(1),
(2), (4) Date: Jan. 17, 2013

(87) PCT Pub. No.: WO2012/011314
PCT Pub. Date: Jan. 26, 2012

(65) Prior Publication Data
US 2013/0123313 A1    May 16, 2013

(30) Foreign Application Priority Data

Jul. 22, 2010 (JP) ................. 2010-165081

(51) Int. Cl.
A61K 31/427 (2006.01)
C07D 417/04 (2006.01)

(52) U.S. Cl.
USPC .......................................... 548/195; 514/371

(58) Field of Classification Search
USPC ....................................... 548/195
See application file for complete search history.

(56) References Cited

U.S. PATENT DOCUMENTS 4,666,931 A    5/1987 Ohishi et al.
5,773,467 A    6/1998 Dyke et al.

FOREIGN PATENT DOCUMENTS

| JP | 62-155269 | 7/1987 |
|---|---|---|
| JP | 2000-501411 | 2/2000 |
| JP | 2005-8631 | 1/2005 |
| JP | 2006-507215 | 3/2006 |
| JP | 2006-225303 | 8/2006 |
| JP | 2007-501796 | 2/2007 |
| WO | WO 03/072561 | 9/2003 |
| WO | WO 2004/078751 | 9/2004 |
| WO | WO 2005/014566 | 2/2005 |
| WO | WO 2006/054793 | 5/2006 |

OTHER PUBLICATIONS

Golub et al., Science, vol. 286, Oct. 15, 1999, pp. 531-537.*
Kuramoto et al. "Preparation of leukotriene $B_4$ inhibitory active 2- and 3-(2-aminothiazol-4-yl)benzo[b]furan derivatives and their growth inhibitory activity on human pancreatic cancer cells". *Organic and Biomolecular Chemistry*, vol. 6, No. 15, pp. 2772-2781 (2008).
Yang et al. "Synthesis of 2-aryl-5-alkyl-7-methoxybenzol[b]furan derivatives". *Chinese Chemical Letters*, vol. 18, No. 4, pp. 380-382 (2007).

* cited by examiner

*Primary Examiner* — Laura L. Stockton
(74) *Attorney, Agent, or Firm* — Hamre, Schumann, Mueller & Larson, P.C.

(57) ABSTRACT

Provided is a novel compound having an effective anti-cancer activity.
The novel compound according to the present invention includes a compound represented by formula (I):

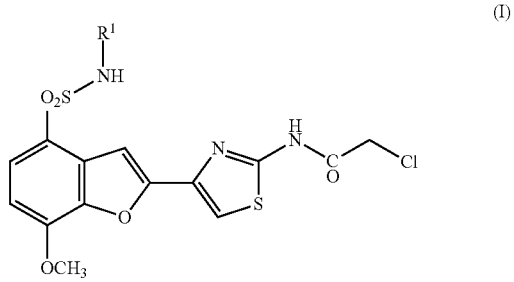

[wherein $R^1$ represents an alkoxyalkyl group having 2 to 6 carbon atoms]
or a pharmaceutically acceptable salt thereof.

6 Claims, 1 Drawing Sheet

MIApaca-2

($\mu$M)

MCF-7

($\mu$M)

BENZOFURANONE COMPOUND AND PHARMACEUTICAL COMPOSITION CONTAINING SAME

FIELD OF THE INVENTION

The present invention relates to a novel benzofuranone compound, a pharmaceutical composition containing the compound as an active ingredient, and a method for producing a novel benzofuran compound.

DESCRIPTION OF THE RELATED ART

Various anti-cancer agents have been developed.

WO 2006/054793 discloses a benzofuran compound useful as a prophylactic or therapeutic agent for cancer, which has a leukotriene inhibition activity, particularly a BLT2 antagonistic inhibition activity.

JP 2006-507215 A and JP 2007-501796 A disclose benzofuran and benzothiophene derivatives for treating hyper proliferative disorders.

On the other hand, it is found that compounds each having a benzofuran skeleton have various pharmacological activities.

WO 2004/078751 discloses a benzofuran derivative useful for the treatment of allergies and inflammatory diseases.

JP 2006-225303 A discloses a benzofuran derivative useful for the prevention and treatment of bone metabolism diseases.

JP 2000-501411 A discloses a benzofuran derivative useful for the treatment of inflammatory diseases and autoimmune diseases.

JP 2005-8631 A discloses a benzofuran derivative having an anti-allergy activity and an anti-inflammation activity.

However, up to now, there is found no effective benzofuran compound having a broad spectrum of anti-cancer activity.

BRIEF SUMMARY OF THE INVENTION

The object of the present invention is to provide a novel compound having a broad spectrum of anti-cancer activity.

The present inventors have made extensive studies for the purpose of solving above problems. As a result, it is found that a specific benzophenone compound has a broad spectrum of anti-cancer activity. This finding leads to the accomplishment of the present invention.

That is, the present invention provides:
[1] a compound represented by formula (I):

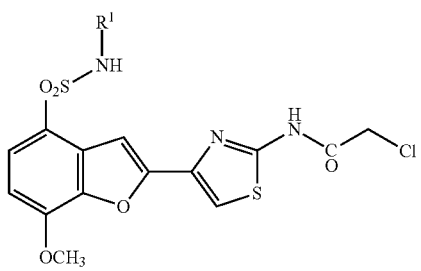

[wherein $R^1$ represents an alkoxyalkyl group having 2 to 6 carbon atoms]
or a pharmaceutically acceptable salt thereof;

[2] the compound or the pharmaceutically acceptable salt thereof according to item [1], wherein the compound represented by formula (I) is selected from the group consisting of 2-chloro-N-[4-(7-methoxy-4-methoxymethylsulfamoyl-benzofuran-2-yl)-thiazol-2-yl]-acetamide, 2-chloro-N-{4-[7-methoxy-4-(2-methoxyethylsulfamoyl)-benzofuran-2-yl]-thiazol-2-yl}-acetamide, 2-chloro-N-{4-[7-methoxy-4-(3-methoxypropylsulfamoyl)-benzofuran-2-yl]-thiazol-2-yl}-acetamide, 2-chloro-N-{4-[7-methoxy-4-(4-methoxybutylsulfamoyl)-benzofuran-2-yl]-thiazol-2-yl}-acetamide, 2-chloro-N-{4-[7-methoxy-4-(5-methoxypentylsulfamoyl)-benzofuran-2-yl]-thiazol-2-yl}-acetamide, 2-chloro-N-[4-(7-methoxy-4-ethoxymethylsulfamoyl-benzofuran-2-yl)-thiazol-2-yl]-acetamide, 2-chloro-N-{4-[7-methoxy-4-(2-ethoxyethylsulfamoyl)-benzofuran-2-yl]-thiazol-2-yl}-acetamide, 2-chloro-N-{4-[7-methoxy-4-(3-ethoxypropylsulfamoyl)-benzofuran-2-yl]-thiazol-2-yl}-acetamide, 2-chloro-N-{4-[7-methoxy-4-(4-ethoxybutylsulfamoyl)-benzofuran-2-yl]-thiazol-2-yl}-acetamide, 2-chloro-N-[4-(7-methoxy-4-propoxymethylsulfamoyl-benzofuran-2-yl)-thiazol-2-yl]-acetamide, 2-chloro-N-{4-[7-methoxy-4-(2-propoxyethylsulfamoyl)-benzofuran-2-yl]-thiazol-2-yl}-acetamide, 2-chloro-N-{4-[7-methoxy-4-(3-propoxypropylsulfamoyl)-benzofuran-2-yl]-thiazol-2-yl}-acetamide, 2-chloro-N-[4-(7-methoxy-4-butoxymethylsulfamoyl-benzofuran-2-yl)-thiazol-2-yl]-acetamide, 2-chloro-N-{4-[7-methoxy-4-(2-butoxyethylsulfamoyl)-benzofuran-2-yl]-thiazol-2-yl}-acetamide and 2-chloro-N-[4-(7-methoxy-4-pentoxymethylsulfamoyl-benzofuran-2-yl)-thiazol-2-yl]-acetamide;

[3] the compound or the pharmaceutically acceptable salt thereof according to item [2], wherein the compound represented by formula (I) is 2-chloro-N-{4-[7-methoxy-4-(2-methoxyethylsulfamoyl)-benzofuran-2-yl]-thiazol-2-yl}-acetamide;

[4] a method for producing a compound represented by formula (I):

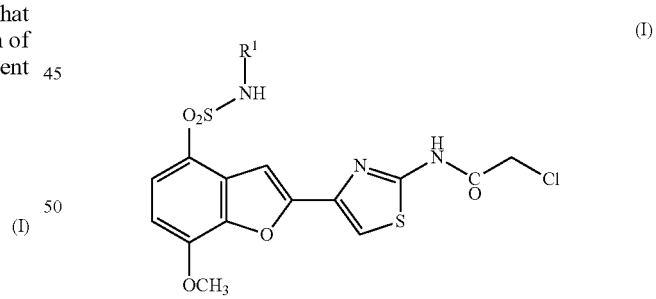

[wherein $R^1$ represents an alkoxyalkyl group having 2 to 6 carbon atoms]
or a pharmaceutically acceptable salt thereof, comprising the steps of:

(1) reacting 2-acetyl-7-methoxybenzofuran with chlorosulfonic acid to produce 2-acetyl-7-methoxybenzofuran-4-sulfonyl chloride;

(2) reacting the resultant sulfonyl chloride compound with an alkoxyalkylamine in the presence of a base to produce a sulfonic acid amide compound represented by formula (II):

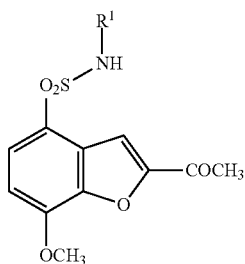

[wherein $R^1$ is as defined above];

(3) reacting the resultant sulfonic acid amide compound with a halogen to halogenate an acetyl group;

(4) reacting the resultant sulfonic acid amide halide with thiourea in the presence of a base under heating conditions to produce a 2-aminothiazolylbenzofuran compound represented by formula (III):

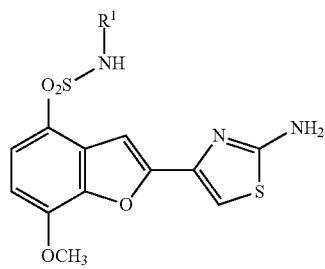

[wherein $R^1$ is as defined above]; and (5) subsequently reacting the resultant 2-aminothiazolylbenzofuran compound with chloroacetyl chloride to produce the compound represented by formula (I);

[5] the method according to item [4], wherein the alkoxyalkylamine to be used in step (2) is selected from the group consisting of methoxymethylamine, 2-methoxyethylamine, 3-methoxypropylamine, 4-methoxybutylamine, 5-methoxypentylamine, ethoxymethylamine, 2-ethoxyethylamine, 3-ethoxypropylamine, 4-ethoxybutylamine, propoxymethylamine, 2-propoxyethylamine, 3-propoxypropylamine, butoxymethylamine, 2-butoxyethylamine and pentoxymethylamine;

[6] a pharmaceutical composition for use in the treatment of cancer, containing a compound represented by formula (I) or a pharmaceutically acceptable salt thereof as an active ingredient; and

[7] the pharmaceutical composition according to item [6], wherein the cancer is selected from the group consisting of pancreatic cancer, breast cancer, brain tumor, glioma, mouth cancer, pharyngeal cancer, laryngeal cancer, lung cancer, esophageal cancer, gastric cancer, kidney cancer, endometrial cancer, cervical cancer, ovarian cancer, retinoblastoma, prostate cancer, testicular tumor, liver cancer, skin cancer, colon cancer and rectum cancer.

EFFECT OF THE INVENTION

According to the present invention, an anti-cancer agent having a broad spectrum of anti-cancer activity can be provided. According to the present invention, a method for producing the anti-cancer agent on an industrial scale can also be provided.

DETAILED DESCRIPTION OF THE INVENTION

Figure 1:
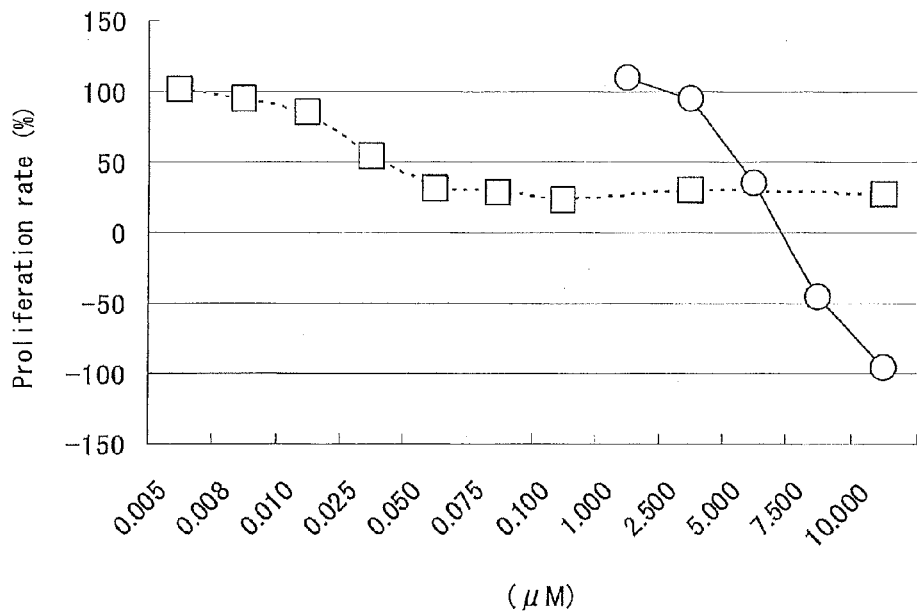
FIG. 1 illustrates a graph showing the inhibition of the proliferation of a cancer cell (MIA PaCa-2) by a compound according to the present invention (-○-) and a known anti-cancer agent Gemzar (-□-).

In a first embodiment, the present invention provides a benzofuran compound represented by formula (I):

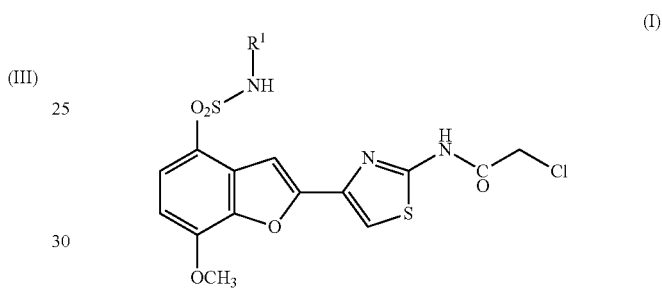

[wherein $R^1$ represents an alkoxyalkyl group having 1 to 6 carbon atoms which may be substituted if desired]
and a pharmaceutically acceptable salt thereof.

In a preferred embodiment, the compound represented by formula (I) includes 2-chloro-N-[4-(7-methoxy-4-methoxymethylsulfamoyl-benzofuran-2-yl)-thiazol-2-yl]-acetamide, 2-chloro-N-{4-[7-methoxy-4-(2-methoxyethylsulfamoyl)-benzofuran-2-yl]-thiazol-2-yl}-acetamide, 2-chloro-N-{4-[7-methoxy-4-(3-methoxypropylsulfamoyl)-benzofuran-2-yl]-thiazol-2-yl}-acetamide, 2-chloro-N-{4-[7-methoxy-4-(4-methoxybutylsulfamoyl)-benzofuran-2-yl]-thiazol-2-yl}-acetamide, 2-chloro-N-{4-[7-methoxy-4-(5-methoxypentylsulfamoyl)-benzofuran-2-yl]-thiazol-2-yl}-acetamide, 2-chloro-N-[4-(7-methoxy-4-ethoxymethylsulfamoyl-benzofuran-2-yl)-thiazol-2-yl]-acetamide, 2-chloro-N-{4-[7-methoxy-4-(2-ethoxyethylsulfamoyl)-benzofuran-2-yl]-thiazol-2-yl}-acetamide, 2-chloro-N-{4-[7-methoxy-4-(3-ethoxypropylsulfamoyl)-benzofuran-2-yl]-thiazol-2-yl}-acetamide, 2-chloro-N-{4-[7-methoxy-4-(4-ethoxybutylsulfamoyl)-benzofuran-2-yl]-thiazol-2-yl}-acetamide, 2-chloro-N-[4-(7-methoxy-4-propoxymethylsulfamoyl-benzofuran-2-yl)-thiazol-2-yl]-acetamide, 2-chloro-N-{4-[7-methoxy-4-(2-propoxyethylsulfamoyl)-benzofuran-2-yl]-thiazol-2-yl}-acetamide, 2-chloro-N-{4-[7-methoxy-4-(3-propoxypropylsulfamoyl)-benzofuran-2-yl]-thiazol-2-yl}-acetamide, 2-chloro-N-[4-(7-methoxy-4-butoxymethylsulfamoyl-benzofuran-2-yl)-thiazol-2-yl]-acetamide, 2-chloro-N-{4-[7-methoxy-4-(2-butoxyethylsulfamoyl)-benzofuran-2-yl]-thiazol-2-yl}-acetamide, and 2-chloro-N-[4-(7-methoxy-4-pentoxymethylsulfamoyl-benzofuran-2-yl)-thiazol-2-yl]-acetamide, and pharmaceutically acceptable salts thereof.

In a second embodiment, the present invention provides a method for producing a compound represented by formula (I).

The benzofuran compound represented by formula (I) can be produced by:

(1) reacting 2-acetyl-7-methoxybenzofuran with chlorosulfonic acid to produce 2-acetyl-7-methoxybenzofuran-4-sulfonyl chloride;

(2) reacting the resultant sulfonyl chloride compound with an alkoxyalkylamine in the presence of a base at 0 to 50° C., preferably 10 to 40° C., more preferably 20 to 30° C., to produce a sulfonic acid amide compound represented by formula (II):

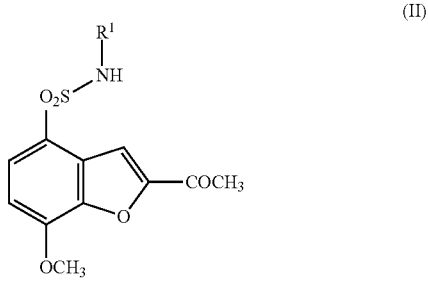

[wherein $R^1$ is as defined above];

(3) reacting the resultant sulfonic acid amide compound with a halogenation reagent at 5 to 50° C., preferably 15 to 40° C., more preferably 20 to 30° C., to monohoganete an acetyl group;

(4) reacting the resultant halide with thiourea in the presence of a base under heating conditions to produce a 2-aminothiazolylbenzofuran compound represented by formula (III):

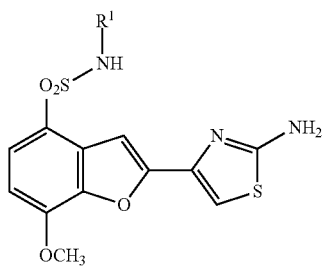

[wherein $R^1$ is as defined above]; and (5) subsequently reacting the resultant 2-aminothiazolylbenzofuran compound with chloroacetyl chloride at 0 to 55° C., preferably 5 to 40° C., more preferably 15 to 30° C.

Examples of the alkoxyalkylamine to be used in step (2) in the production method include methoxymethylamine, 2-methoxyethylamine, 3-methoxypropylamine, 4-methoxybutylamine, 5-methoxypentylamine, ethoxymethylamine, 2-ethoxyethylamine, 3-ethoxypropylamine, 4-ethoxybutylamine, propoxymethylamine, 2-propoxyethylamine, 3-propoxypropylamine, butoxymethylamine, 2-butoxyethylamine and pentoxymethylamine.

Examples of the halogen contained in the halogenation reagent to be used in step (3) in the production method include chlorine, bromine and iodine.

In the production method, a solvent such as acetonitrile, ethanol, methanol, chloroform, hexane and ethyl acetate can be used in reactions, liquid-liquid partition, recrystallization and so on.

Examples of the base include organic bases such as pyridine, diethylamine and triethylamine, alkali metal alkoxides such as sodium methoxide and sodium ethoxide, and inorganic bases such as sodium hydroxide and potassium hydroxide.

In a third embodiment, the present invention provides a pharmaceutical composition for use in the treatment of cancer, which contains a compound represented by formula (I) or a pharmaceutically acceptable salt thereof as an active ingredient. The pharmaceutical composition according to the present invention can be used as, for example, a therapeutic agent or a prophylactic agent for cancer.

The pharmaceutical composition according to the present invention can be administered as an anti-cancer agent in an oral or parenteral route. Therefore, a compound which can be metabolized into the compound according to the present invention or a compound that is substantially the same as the compound according to the present invention in vivo, i.e., a prodrug, is also included within the scope of the compound according to the present invention.

The pharmaceutical composition according to the present invention can be prepared using the compound (I) or a pharmaceutically acceptable salt thereof as an active ingredient and a pharmaceutical carrier. The pharmaceutical carrier may be selected properly depending on the dosage form of the preparation, and examples of the pharmaceutical carrier include starch, lactose, hydroxypropyl cellulose, hydroxypropyl methyl cellulose, polyvinyl pyrrolidone, aluminum stearate and magnesium stearate.

When the pharmaceutical composition according to the present invention is administered in an oral route, the pharmaceutical composition can be administered in the dosage form of, for example, a tablet, a capsule, a syrup and a suspension. Meanwhile, when the pharmaceutical composition according to the present invention is administered in a parenteral route, the pharmaceutical composition can be administered in the dosage form of a solution, an emulsion, a suspension or the like as an injectable preparation, a transdermal preparation or a spraying preparation, or in a dosage form of a tablet or the like as a suppository.

The pharmaceutical composition according to the present invention can also be prepared in the form of a sustained-release preparation. The dosage form of this type can be prepared by mixing a carrier, an excipient, a binder, a stabilizing agent and the like which are used conventionally with the active ingredient by any known preparation method. When the pharmaceutical composition is used in an injectable dosage form, a buffering agent, a dissolution aid, a tonicity adjusting agent and the like may be added.

Examples of the cancer to be treated with the pharmaceutical composition include pancreatic cancer, breast cancer, brain tumor, glioma, mouth cancer, pharyngeal cancer, laryngeal cancer, lung cancer, esophageal cancer, gastric cancer, kidney cancer, endometrial cancer, cervical cancer, ovarian cancer, retinoblastoma, prostate cancer, testicular tumor, liver cancer, skin cancer, colon cancer and rectum cancer in a mammal, preferably a human body.

When the pharmaceutical composition according to the present invention is administered as an anti-cancer agent, the dosage and the frequency of administration are varied depending on various factors including the types of diseases to be treated, the conditions, ages, body weights, sexes and the like of patients, the routes of administrations and dosage forms. When the pharmaceutical composition is administered in an oral route, the pharmaceutical composition can be administered generally in an amount of about 1 to 3000 mg, preferably about 1 to 1000 mg or about 500 to 1500 mg, more preferably about 10 to 500 mg, in terms of the content of the compound (I), which is the active ingredient, per day in a single dose or divided doses for adults. When the pharmaceutical composition is administered in the form of an injectable preparation, the injectable preparation can be generally administered in an amount of about 1 to 3000 mg, preferably about 1 to 1000 mg or about 500 to 1500 mg, more preferably about 10 to 500 mg, in terms of the content of the compound (I) per day in a single dose or divided doses for adults.

The pharmaceutical composition according to the present invention can be administered in various manners. For example, the pharmaceutical composition can be administered at the above-mentioned dosage continuously for several weeks to several months or, alternatively, can be administered continuously for several weeks to several months and is then administered again after the elapse of a predetermined wash-out period.

The present invention is explained more in detail on the basis of Examples. However, the present invention is not limited by the Examples.

EXAMPLE 1

Production Example

2-Acetyl-7-methoxybenzofuran (0.15 g) (0.79 mmol) was added by portions to chlorosulfonic acid (about 2 mL) which had been cooled to 0° C. in ice while agitation. After 40 minutes, the progress of the reaction was confirmed by thin-layer chromatography (an E. Merck silica gel plate (0.5 mm, 60E-254), a developing solution $CHCl_3$:AcOEt=3:2). As a result, the disappearance of the raw materials was confirmed, and therefore the reaction was terminated. The resultant product was poured on ice and then extracted with chloroform, the resultant extract was dried on $MgSO_4$ and then filtered, and the solvent was distilled away from a filtrate, thereby yielding 2-acetyl-7-methoxybenzofuran-4-sulfonyl chloride in the form of a white solid.

Elemental analysis: as $C_{11}H_9ClO_5S$
calculated: C, 45.86; H, 3.14
found: C, 45.74; H, 3.21
Mass spectrometry:
calculated: 288.70
found: 287.99.

Dried chloroform (4 mL), triethanolamine (0.42 mL) (TEA, 0.31 g, 3.02 mmol) and 2-methoxyethylamine (0.15 mL) (0.13 g, 1.71 mmol) were mixed together, 2-acetyl-7-methoxybenzofuran-4-sulfonyl chloride that had been dissolved in dried dichloromethane (10 mL) was added to the resultant mixture dropwisely, and the resultant mixture was allowed to react with one another at 26° C. After 90 minutes, the progress of the reaction was confirmed by thin-layer chromatography (an E. Merck silica gel plate (0.5 mm, 60E-254), a developing solution $CHCl_3$:AcOEt=5:2). As a result, the disappearance of the raw materials was confirmed, and therefore the reaction was terminated. The resultant product was poured on ice and then extracted with chloroform, the resultant extract was dried on $MgSO_4$ and then filtered, and the solvent was then distilled away from the resultant filtrate, thereby yielding yellow crystals (0.25 g). The crystals were recrystallized from hexane and ethyl acetate, thereby yielding 2-acetyl-7-methoxybenzofuran-4-sulfonic acid (2-methoxyethyl)-amide (0.12 g) in the form of yellow crystals (yield: 46.2%).

Yellow crystals: 0.12 g (46.2%)
$R_f$=0.32 ($CHCl_3$:AcOEt=5:2)
m.p. 153.6-155.1° C.
Elemental analysis: as $C_{14}H_{17}NO_6S$
calculated: C, 51.37; H, 5.23; N, 4.28
found: C, 51.28; H, 5.28; N, 4.23.
$^1$H-NMR (500 MHz, $CDCl_3$)δ:2.65 (3H, s, —$COCH_3$), 3.11 (2H, q, J=5.5 Hz, —$SO_2NHCH_2CH_2OCH_3$), 3.23 (3H, s, —$SO_2NHCH_2CH_2OCH_3$), 3.37 (2H, t, J=5.1 Hz, —$SO_2NHCH_2CH_2OCH_3$), 4.09 (3H, s, —$OCH_3$), 4.89 (1H, t, J=6.0 Hz, —$SO_2NHCH_2CH_2OCH_3$), 6.98 (1H, d, J=8.3 Hz, Bf-6H), 7.81 (1H, d, J=8.2 Hz, Bf-5H), 7.87 (1H, s, Bf-3H).
EIMS (70 eV) m/z (rel. int., %):327 ($M^+$, 19.35), 282 (15.68), 253 (79.83), 189 (34.55), 86 (100.00).

2-Acetyl-7-methoxybenzofuran-4-sulfonic acid (2-methoxyethyl)-amide (1.5 g) (4.59 mmol) was added to and dissolved in dried chloroform (10 mL) at room temperature (25° C.), and then dried chloroform (10 mL) into which $Br_2$ (0.72 g) (4.59 mmol) had been added was added to the resultant mixture dropwisely. After 15 minutes, the progress of the reaction was confirmed by thin-layer chromatography (an E. Merck silica gel plate (0.5 mm, 60F-254), a developing solution: $CHCl_3$:AcOEt=5:2). As a result, the disappearance of the raw materials was confirmed, and therefore the reaction was terminated. The resultant product was poured into an aqueous saturated $NaHCO_3$ solution, and the resultant solution was agitated and then extracted with chloroform. The resultant extract was washed with brine, the wash solution was dried on $MgSO_4$, and then the solvent was distilled away from the resultant solution, thereby yielding a yellow solid (1.88 g). The solid was recrystallized from hexane and ethyl acetate, thereby yielding 2-(2-bromoacetyl)-7-methoxybenzofuran-4-sulfonic acid (2-methoxyethyl)-amide (0.94 g) in the form of whitish yellow crystals (yield: 51%).

Whitish yellow crystals: 0.94 g (51%)
$R_f$=0.45 ($CHCl_3$:AcOEt=5:2)
m.p. 154.7-157.6° C.
EIMS (70 eV) m/z (rel. int., %):407 (M+2, 29.27), 405 ($M^+$, 27.86), 362 (35.24), 333 (100.00).

2-(2-Bromoacetyl)-7-methoxybenzofuran-4-sulfonic acid (2-methoxyethyl)-amide (0.3 g) (0.74 mmol) and thiourea (0.07 g) (0.89 mmol) were added to absolute ethanol (10 mL) to which sodium ethoxide had been added, and the resultant mixture was agitated and then refluxed. After 5 days, the progress of the reaction was confirmed by thin-layer chromatography (an E. Merck silica gel plate (0.5 mm, 60F-254), a developing solution: $CHCl_3$:MeOH=5:2). As a result, the disappearance of the raw materials was confirmed, and therefore the reaction was terminated. The solvent was distilled away from the reaction product, and the residue was recrystallized from methanol, thereby yielding 2-(2-amino thiazol-4-yl)-7-methoxybenzofuran-4-sulfonic acid (2-methoxyethyl)-amide (0.12 g) in the form of whitish yellow crystals (yield: 39%).

Yellow crystals: 0.12 g (39%)
$R_f$=0.89 ($CHCl_3$:MeOH=5:2)
m.p. 205.7-207.3° C.
Elemental analysis: as $C_{15}H_{17}N_3O_5S_2$
calculated: C, 46.98; H, 4.47; N, 10.96
found: C, 47.00; H, 4.39; N, 10.77.
$^1$H-NMR (400 MHz, DMSO-D6)δ:2.88 (2H, t, J=5.9 Hz, —$SO_2NHCH_2CH_2OCH_3$), 3.10 (3H, s, —$SO_2NHCH_2CH_2OCH_3$), 3.25 (2H, t, J=5.9 Hz, —$SO_2NHCH_2CH_2OCH_3$), 4.03

(3H, s, —OCH$_3$), 7.08 (1H, d, J=8.4 Hz, Bf-6H), 7.15 (1H, s, Bf-3H or thiazol-H), 7.21 (2H, s, —NH$_2$), 7.32 (1H, s, Bf-3H or thiazol-H), 7.63 (1H, d, J=8.4 Hz, Bf-5H), 7.70 (1H, br-s, —SO$_2$NH—).

EIMS (70 eV) m/z (rel. int., %):383 (M$^+$, 85.57), 309 (80.39), 245 (100.00).

2-(2-Aminothiazol-4-yl)-7-methoxybenzofuran-4-sulfonic acid (2-methoxyethyl)-amide (0.22 g), (0.57 mmol) was added to anhydrous tetrahydrofuran (14 mL), the resultant mixture was agitated, and then chloroacetyl chloride (0.05 mL) (0.07 g, 0.68 mmol) and TEA (0.08 mL) (0.06 g, 0.57 mmol) were added thereto at room temperature (23° C.). After 17 hours, the progress of the reaction was confirmed by thin-layer chromatography. As a result, it was found that the raw materials were remained in small amounts. Then, chloroacetyl chloride (0.05 mL) was added to the reaction solution, and the reaction was further continued. After 1 hour, the progress of the reaction was confirmed by thin-layer chromatography (an E. Merck silica gel plate (0.5 mm, 60F-254), a developing solution: CHCl$_3$:AcOEt=7:3). As a result, it was found that almost all of the raw materials disappeared, and therefore the reaction was terminated. The reaction product was poured into water, the resultant mixture was agitated, and the precipitated solid was filtered by suction, thereby yielding a yellowish white solid (0.23 g). The solid was recrystallized from hexane and ethyl acetate, thereby yielding 2-chloro-N-{4-[7-methoxy-4-(2-methoxyethylsulfamoyl)-benzofuran-2-yl]-thiazol-2-yl}-acetamide (0.17 g) in the form of whitish yellow crystals (yield: 65%), which was named "MU-1497".

Whitish yellow crystals: 0.17 g (65%)
R$_f$=0.83 (CHCl$_3$:AcOEt=7:3)
m.p. 182.0-184.5° C.
Elemental analysis: as C$_{17}$H$_{18}$ClN$_3$O$_6$S$_2$
calculated: C, 44.39; H, 3.94; N, 9.14
found: C, 44.38; H, 3.99; N, 8.96.

$^1$H-NMR (400 MHz, CDCl$_3$)δ:3.11 (2H, q, J=5.5 Hz, —SO$_2$NHCH$_2$CH$_2$OCH$_3$), 3.21 (3H, s, —SO$_2$NHC$\overline{H_2}$CH$_2$OCH$_3$), 3.34 (2H, t, J=5.1 Hz, —SO$_2$NHCH$_2$CH$_2$OC$\overline{H_3}$), 4.09 (3H, s, —OCH$_3$),4.31 (2H, s, —NHCOC$\overline{H_2}$Cl), 4.93 (1H, t, J=6.0 Hz, —SO$_2$N HCH$_2$CH$_2$OC$\overline{H_3}$), 6.76 (1H, d, J=8.4 Hz, Bf-6H), 7.49 (1H, s, $\overline{B}$f-3H or thiazol-H), 7.55 (1H, s, Bf-3H or thiazol-H), 7.75 (1H, d, J=8.4 Hz, Bf-5H), 9.77 (1H, s, —NHCOCH$_2$Cl).

EIMS (70 eV) m/z (rel. int., %): 461 ($\overline{M}$+2, 33.19), 459 (M$^+$, 74.83), 321 (100.00).

EXAMPLE 2

Cancer Cell Proliferation Inhibition Test

Examination was made on the cell proliferation inhibition activity of the newly synthesized compound (MU-1497) on a human pancreatic cancer cell (MIA PaCa-2) and a human breast cancer cell (MCF-7) in vitro. As positive control substances, 5-fluorouracil (5-FU, Sigma) and gemcitabine hydrochloride (Gemzar, GEM, Eli Lilly Japan K.K.), were tested. The experiment was carried out in accordance with the method carried out by the Commission of Screening for Carcinostatic Agents of the Ministry of Education, Culture, Sports, Science and Technology. With respect to each of experiment groups, the experiment was repeated nine times and an average value was determined. Specifically, each type of cultured cells were seeded into a 96-well microplate at a density of 1×10$^4$ cells per well (5.0×10$^4$ cells/mL, 200 μL), the cells were cultured under 5% CO$_2$ at 37° C. for 24 hours, the culture medium was replaced by a culture medium containing the compound (180 μL, the maximum dose of each of the compound was 10 μM, and the final concentration of dimethylsulfoxide (DMSO, Sigma) was adjusted to 0.25%), and the culture was further continued under the same conditions for 72 hours. In this experiment, Dulbecco's modified Eagle's medium (D-MEM, Wako Pure Chemical Industries, Ltd.) was used for the culture of MIA PaCa-2, and Eagle's minimal essential medium (E-MEM, Wako Pure Chemical Industries, Ltd.) was used for the culture of MCF-7.

After the completion of the culture, alamar blue (20 μL) (Iwaki Glass Co., Ltd.) was added to the culture medium, the resultant mixture was agitated, the culture was then carried out for 3 hours, and fluorescence values were determined on a fluorescence plate reader (Spectra Max M5 (Nihon Molecular Devices Corporation)) at an excitation wavelength of 530 nm and a fluorescence wavelength of 590 nm.

The fluorescence values immediately before the action of each of the compounds were determined by replacing the culture medium, adding alamar blue (20 μL) immediately after the replacement of the culture medium, agitating the resultant mixture, carrying out the culture for 3 hours, and measuring the fluorescence values on a fluorescence plate reader.

On the basis of the measurement values thus obtained, Tz (the state of the cultured cells immediately before the action of the compound), GI$_{50}$ (the concentration of the compound required for inhibiting the proliferation of the cultured cells by 50% relative to the proliferation of the cultured cells in the presence of each of the control compounds), TGI (the concentration of the compound required for inhibiting the proliferation of the cells in such a manner that the number of the cells became the same as Tz), LC$_{50}$ (the concentration of the compound required for decreasing the number of the cells to 50% of Tz) and the proliferation rate (the rate of the proliferation of the cultured cells from the time pint of the action of the compound until the time point of the measurement of fluorescence) were determined. The results are shown in FIG. 1 and Table 1.

Due to the problem of the solubility of each of the compounds, the maximum concentration was set at 10 μM. With respect to a compound for which an LC$_{50}$ value could not be calculated, the maximum concentration was set to a value higher than 10 μM.

As illustrated in FIG. 1, MU-1497 which is the compound according to the present invention exhibited a cytotoxic or cell proliferation inhibition activity on MIA PaCa-2 at a concentration of 2.5 μM or higher, wherein the proliferation rate when applied at a concentration of 10 μM (the maximum dose) was −95.39%. In contrast, gemcitabine hydrochloride which is a known anti-cancer agent exhibited a cytotoxic or cell proliferation inhibition activity on MIA PaCa-2 at a concentration of 0.0075 μM or higher, wherein the proliferation rate when applied at a concentration of 10 μM was 26.47%.

Figure 2:
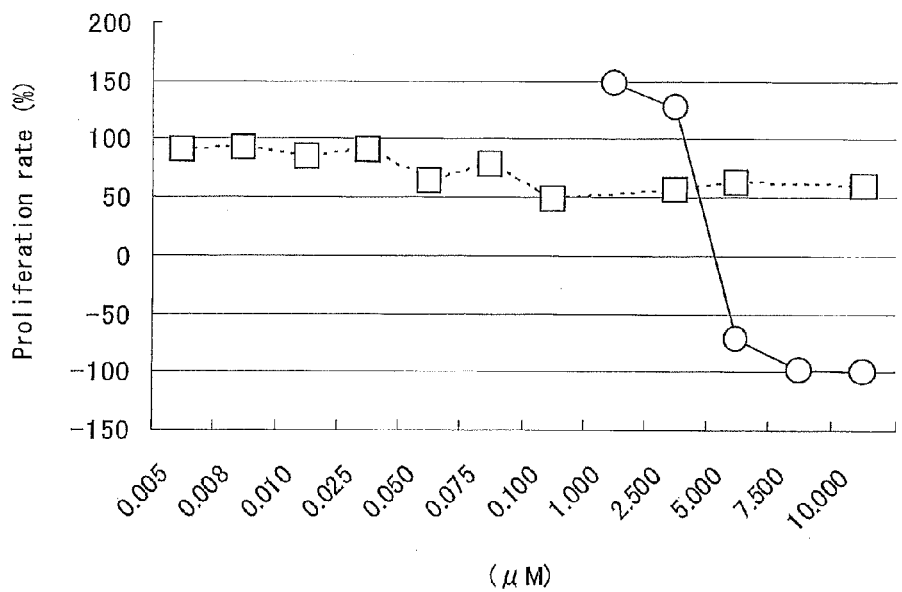
FIG. 2 illustrates a graph showing the inhibition of the proliferation of a cancer cell (MCF-7) by a compound according to the present invention (-○-) and the known anti-cancer agent Gemzar (-□-).

Further, as illustrated in FIG. 2, MU-1497 which is the compound according to the present invention exhibited a cytotoxic or cell proliferation inhibition activity on MCF-7 at a concentration of 5.0 μM or higher, wherein the proliferation rate when applied at a concentration of 10 μM (the maximum dose) was −99.71%. In contrast, gemcitabine hydrochloride exhibited a cytotoxic or cell proliferation inhibition activity on MCF-7 at a concentration of 0.005 μM or higher, wherein the proliferation rate when applied at a concentration of 10 ηM was 59.52%.

TABLE 1

|  | GI$_{50}$ | | TGI | | LC$_{50}$ | |
| --- | --- | --- | --- | --- | --- | --- |
|  | MIA PaCa-2 | MCF-7 | MIA PaCa-2 | MCF-7 | MIA PaCa-2 | MCF-7 |
| MU-1497 | 4.22 | 3.82 | 6.15 | 4.70 | 8.07 | 5.81 |
| 5-FU | >10 | >10 | >10 | >10 | >10 | >10 |
| GEM | 0.035 | >10 | >10 | >10 | >10 | >10 |

As shown in Table 1, MU-1497 which is the compound according to the present invention exhibited a cytotoxic or cell proliferation inhibition activity on both MIA PaCa-2 cells and cultured MCF-7 cells (GI$_{50}$ values: 4.22 μM and 3.82 μM, respectively). In contrast, 5-fluorouracil which is a known anti-cancer agent did not exhibit either of these activities on either MIA PaCa-2 or MCF-7, and gemcitabine hydrochloride exhibited a cytotoxic or cell proliferation inhibition activity on MIA PaCa-2 but did not exhibit either of these activities on MCF-7.

From these test results, among the compounds used for this test, MU-1497 was confirmed as having a cytotoxic or cell proliferation inhibition activity on both MIA PaCa-2 and MCF-7. In contrast, gemcitabine hydrochloride was confirmed as having a cytotoxic or cell proliferation inhibition activity on MIA PaCa-2 at a concentration of 0.0075 μM and on MCF-7 at a concentration of 0.005 μM, but the increase in the activity was not observed at a concentration of 0.05 μM or higher.

Thus, the cytotoxic or cell proliferation inhibition activity of MU-1497 which is the compound according to the present invention was observed in a higher concentration range compared with that of gemcitabine hydrochloride which is a known anti-cancer agent, but it was demonstrated that the intensities of the maximum reactions on both of the cells were greater than those of gemcitabine hydrochloride. Consequently, it is found that a novel anti-cancer agent having a higher carcinostatic activity than those of known anti-cancer agents could be produced according to the present invention.

INDUSTRIAL APPLICABILITY

The present invention relates to the field of medicines. More specifically, the present invention relates to the field of a novel anti-cancer agent, and relates to an anti-cancer agent having a more potent carcinostatic activity and a broader spectrum of anti-cancer activity compared with those of known anti-cancer agents.

The invention claimed is:

1. A compound represented by formula (I):

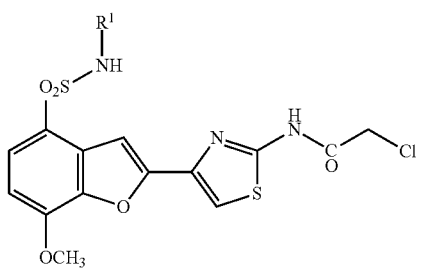

(I)

wherein R$^1$ represents an alkoxyalkyl group having 2 to 6 carbon atoms,
or a pharmaceutically acceptable salt thereof.

2. The compound or the pharmaceutically acceptable salt thereof according to claim 1, wherein the compound represented by formula (I) is selected from the group consisting of 2-chloro-N-[4-(7-methoxy-4-methoxymethylsulfamoyl-benzofuran-2-yl)-thiazol-2-yl]-acetamide, 2-chloro-N-{4-[7-methoxy-4-(2-methoxyethylsulfamoyl)-benzofuran-2-yl]-thiazol-2-yl}-acetamide, 2-chloro-N-{4[7-methoxy-4-(3-methoxypropylsulfamoyl)-benzofuran-2-yl]-thiazol-2-yl}-acetamide, 2-chloro-N-{4-[7-methoxy-4-(4-methoxybutylsulfamoyl)-benzofuran-2]-thiazol-2-yl}-acetamide, 2-chloro-N-{4-[7-methoxy-4-(5-methoxypentylsulfamoyl)-benzofuran-2-yl]-thiazol-2-yl}acetamide, 2-chloro-N-[4-(7-methoxy-4-ethoxymethylsulfamoyl-benzofuran-2-yl)-thiazol-2-yl]-acetamide, 2-chloro-N-{4-[7-methoxy-4-(2-ethoxyethylsulfamoyl)-benzofuran-2-yl]-thiazol-2-yl}-acetamide, 2-chloro-N-{4-[7-methoxy-4-(3-ethoxypropylsulfamoyl)-benzofuran-2-yl]-thiazol-2-yl}1-acetamide, 2-chloro-N-{4-[7-methoxy-4-(4-ethoxybutylsulfamoyl)-benzofuran-2-yl]-thiazol-2-yl}-acetamide, 2-chloro-N-[4-(7-methoxy-4-propoxymethylsulfamoyl-benzofuran-2-yl)-thiazol-2-yl]-acetamide, 2-chloro-N-{4-[7-methoxy-4-(2-propoxyethylsulfamoyl)-benzofuran-2-yl]-thiazol-2-yl}-acetamide, 2-chloro-N-{4-[7-methoxy-4-(3-propoxypropylsulfamoyl)-benzofuran-2-yl]-thiazol-2-yl}-acetamide, 2-chloro-N-[4(7-methoxy-4-butoxymethylsulfamoyl-benzofuran-2-yl)-thiazol-2-yl]-acetamide, 2-chloro-N-{4[7-methoxy-4-(2-butoxyethylsulfamoyl)-benzofuran-2-yl]-thiazol-2-yl}-acetamide and 2-chloro-N-[4-(7-methoxy-4-pentoxymethylsulfamoyl-benzofuran-2-yl)-thiazol-2-yl]-acetamide.

3. The compound or the pharmaceutically acceptable salt thereof according to claim 2, wherein the compound represented by formula (I) is 2-chloro-N-{4-[7-methoxy-4-(2-methoxyethylsulfamoyl)-benzofuran-2-yl]-thiazol-2-yl}-acetamide.

4. A method for producing a compound represented by formula (I):

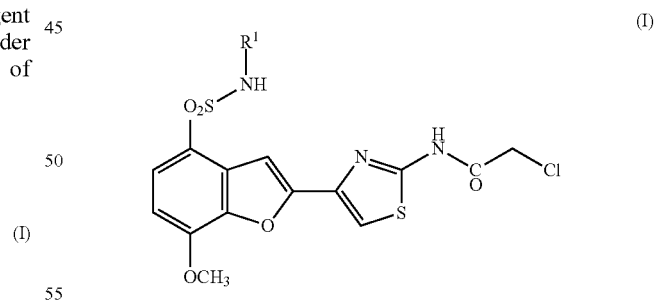

(I)

wherein R$^1$ represents an alkoxyalkyl group having 2 to 6 carbon atoms,
or a pharmaceutically acceptable salt thereof, comprising the steps of:
  (1) reacting 2-acetyl-7-methoxybenzofuran with chlorosulfonic acid to produce 2-acetyl-7-methoxybenzofuran-4-sulfonyl chloride;
  (2) reacting the resultant sulfonyl chloride compound with an alkoxyalkylamine in the presence of a base to produce a sulfonic acid amide compound represented by formula (II):

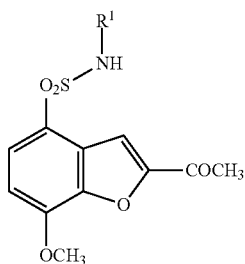

wherein R¹ is as defined above;
(3) reacting the resultant sulfonic acid amide compound with a halogen to halogenate an acetyl group;
(4) reacting the resultant sulfonic acid amide halide with thiourea in the presence of a base under heating conditions to produce a 2-aminothiazolylbenzofuran compound represented by formula (III):

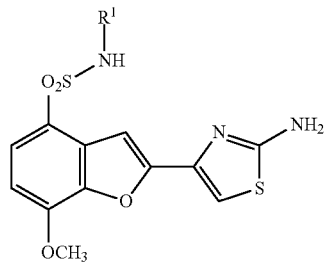

wherein R¹ is as defined above; and
(5) subsequently reacting the resultant 2-aminothiazolylbenzofuran compound with chloroacetyl chloride to produce the compound represented by formula (I).

5. The method according to claim 4, wherein the alkoxyalkylamine to be used in step (2) is selected from the group consisting of methoxymethylamine, 2-methoxyethylamine, 3-methoxypropylamine, 4-methoxybutylamine, 5-methoxypentylamine, ethoxymethylamine, 2-ethoxyethylamine, 3-ethoxypropylamine, 4-ethoxybutylamine, propoxymethylamine, 2-propoxyethylamine, 3-propoxypropylamine, butoxymethylamine, 2-butoxyethylamine and pentoxymethylamine.

6. A pharmaceutical composition for use in the treatment of cancer, wherein the cancer is selected from human pancreatic cancer and human breast cancer, comprising a compound represented by formula (I) or a pharmaceutically acceptable salt thereof as an active ingredient

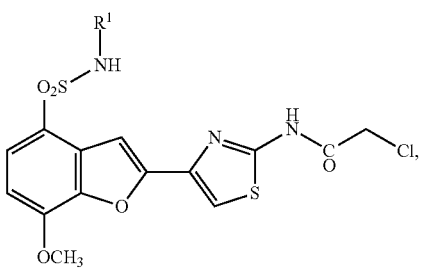

wherein R¹ represents an alkoxyalkyl group having 2 to 6 carbon atoms.

\* \* \* \* \*

UNITED STATES PATENT AND TRADEMARK OFFICE
CERTIFICATE OF CORRECTION

PATENT NO. : 8,563,743 B2  
APPLICATION NO. : 13/810796  
DATED : October 22, 2013  
INVENTOR(S) : Ohishi et al.

It is certified that error appears in the above-identified patent and that said Letters Patent is hereby corrected as shown below:

In the Specification

Column 4, line 39, delete "yl) -thiazol" and insert -- yl)-thiazol --.

Column 8, line 67, delete " $\underline{CH_3}$. " and insert -- $\underline{CH_3}$ --.

Column 9, line 8, after "(0.22 g)" delete ",".

Column 10, line 67, delete "ηM" and insert -- μM --.

In the Claims

Column 12, line 7, in Claim 2, delete "{4[7" and insert -- {4-[7 --.

Column 12, line 11, in Claim 2, delete "2]-thiazol" and insert -- 2-yl]-thiazol --.

Column 12, line 14, in Claim 2, delete "yl}acetamide," and insert -- yl}-acetamide, --.

Column 12, line 19, in Claim 2, delete "yl}1-" and insert -- yl}- --.

Column 12, line 29, in Claim 2, delete "[4(7" and insert -- [4-(7 --.

Column 12, line 31, in Claim 2, delete "{4[7" and insert -- {4-[7 --.

Signed and Sealed this  
Twentieth Day of May, 2014

Michelle K. Lee  
*Deputy Director of the United States Patent and Trademark Office*